United States Patent [19]

Campbell

[11] 4,156,790

[45] May 29, 1979

[54] ISOMERIZATION OF DIHYDROXYDIPHENYL COMPOUNDS

[75] Inventor: John R. Campbell, Clifton Park, N.Y.

[73] Assignee: General Electric Company, Schenectady, N.Y.

[21] Appl. No.: 895,091

[22] Filed: Apr. 10, 1978

[51] Int. Cl.² ............................................. C07C 37/00
[52] U.S. Cl. .................................................. 568/726
[58] Field of Search ................................. 568/723, 726

[56] References Cited

U.S. PATENT DOCUMENTS

| 4,097,538 | 6/1978 | Factor et al. | 568/723 |
| 4,102,934 | 7/1978 | Quinn | 568/726 |
| 4,105,857 | 8/1978 | Campbell et al. | 568/726 |
| 4,107,442 | 8/1978 | Quinn | 568/726 |
| 4,117,018 | 9/1978 | Cleveland et al. | 568/726 |

*Primary Examiner*—Norman Morgenstern
*Attorney, Agent, or Firm*—Joseph T. Cohen; Charles T. Watts

[57] ABSTRACT

Isomerization of an ortho, para-isomer of a dihydroxydiphenyl chloroethylene compound to the corresponding para, para-isomer can be effected by treatment of the former with trifluoromethanesulfonic acid in the presence of phenol.

6 Claims, No Drawings

ISOMERIZATION OF DIHYDROXYDIPHENYL COMPOUNDS

This invention is concerned with a process for isomerizing a certain class of dihydroxydiphenyl compounds. More particularly, the invention is concerned with the process for converting an ortho, para-isomer of the formula

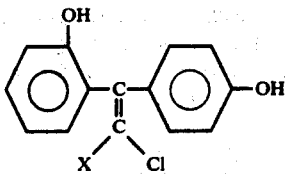

to the para, para-isomer of the formula

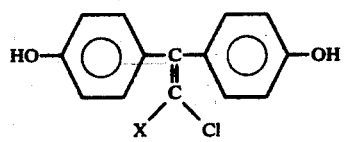

where X is a member selected from the class consisting of hydrogen and chlorine, which process comprises contacting the ortho, para-isomer with trifluoromethanesulfonic acid in the presence of phenol for a time and at a temperature sufficient to convert a substantial amount of the ortho, para-isomer to the para, para-isomer.

The compound 1,1-dichloro-2,2-bis(4-hydroxyphenyl) ethylene having the formula

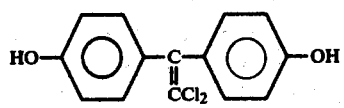

is a valuable monomer in the preparation of certain polyester resins. More particularly, this compound of formula III can be treated with either phosgene or diphenyl carbonate to make polycarbonate resins comprising recurring units of the formula

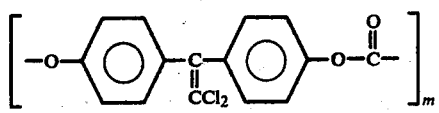

where m is a whole number greater than 2. These resins have exceptional flame-resistant and flame-retardant characteristics. Generally, the compound of formula III required to make these polycarbonate resins is first obtained in the precursor form by reacting phenol and chloral in the presence of an acidic condensing agent to form the trichloro-ethane derivative having the formula

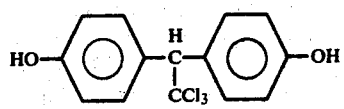

This trichloro-ethane derivative is then dehydrohalogenated with, for instance, ammonia or an alkali-metal hydroxide to form the dichloromethylene compound of formula III. In the preparation of the trichloro-ethane compound, there are also formed other compounds or isomers including the ortho, para-isomer having the formula

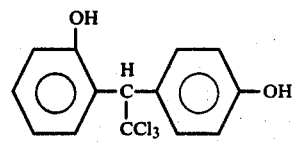

in addition to the trichloro-ethane derivative of formula IV. Another compound which is formed as a result of the dehydrohalogenation step is the chloroethylene compound corresponding to the general formula

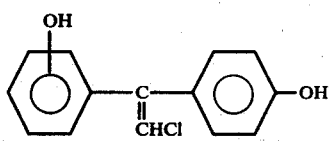

where the floating hydroxy group is either ortho or para to the chloroethylene grouping.

In the preparation of the aforementioned polycarbonates, for optimum properties it is important that the dichloroethylene compound of formula III be essentially the only dihydroxydiphenyl compound present. If there is any significant amount of the ortho, para-derivative, this could adversely affect the properties of the polycarbonate resin prepared therefrom. Generally, the ortho, para-isomers of formula I are the predominate impurities in the dichloroethylene monomer of formula III which is used for making the polycarbonate resins. The dichloroethylene compounds, whether the ortho, para-isomer or the para, para-isomer, are the direct result of the dehydrohalogenation of the corresponding higher chlorinated dihydroxydiphenyl compounds which are obtained in the initial reaction between the phenol and chloral.

It is accordingly one of the objectives of this invention to reduce to a minimum the amount of ortho, para-isomers present with the dichloroethylene compound of formula III used to make polycarbonate resins.

It is a still further object of the invention to reduce or eliminate the presence, particularly of the ortho, para-isomer of the formula

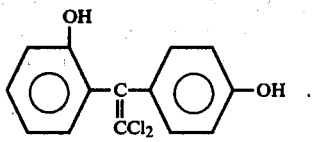

Other objects of the invention will become apparent from the following description.

I have now discovered that I can treat an ortho, para-isomer of the generic formula I with trifluoromethanesulfonic acid in phenol and convert the ortho, para-isomer in some instances to almost quantitative yield to the para, para-isomer of formula II. If the conversion to the para, para-isomer is not absolutely complete, the small amount of the ortho, para-isomer remaining in the para, para-isomer is so small as to have little if any effect on the properties of polymers prepared by treatment of the dichloroethylene para, para-isomer with the phosgenating agent.

It was entirely unexpected and in no way could have been predicted that the trifluoromethanesulfonic acid when applied to the ortho, para-isomer of formula I would be so effective in converting the latter to the para, para-isomer since when the same procedure was applied to the saturated precursor, such as that of formula V, employing the trifluoromethanesulfonic acid in phenol, only a small amount of isomerization occurred.

It was also surprising to find that other strong acids, such as a mixture of $HF/BF_3$ with phenol, gave much smaller amounts of isomerization and also led to decomposition of the reactants and a substantial amount of undesirable by-product formation. Still other strong acids, such as trifluoroacetic acid and $H_2SO_4$, also failed to give the desirable results obtained by using the trifluoromethanesulfonic acid.

In carrying out the treatment of the ortho, para-isomer (whichever one is used) with the trifluoromethanesulfonic acid in phenol, fairly moderate temperatures can be employed. Generally, temperatures ranging from about $-10°$ C. to about below the decomposition point of either the reactant or the formed para, para-isomer should be employed. I have found that within the range of $-10°$ to about 50° C., optimum results are attained. As the temperature is increased, additional degradation and by-product formation occurs. In all instances, I have found it helpful to employ an inert atmosphere, e.g., nitrogen, helium, etc., within which to carry out the reaction.

The amount of phenol used with the ortho, para-isomer can be varied widely but generally should be at least equal, on a weight basis, to the weight of the ortho, para-isomer. I have found that, on a weight basis, one can employ from about 1 to 25 or more parts of phenol per part of the orth, para-isomer. If isomerization is intended for a mixture containing both the para, para-isomer and the ortho, para-isomer, the amount of phenol used is generally based on the amount of ortho, para-isomer present in the mixture.

The amount of trifluoromethanesulfonic acid used is not critical and can also be varied quite widely. Generally, on a weight basis, one can employ from about 0.5 to 25 parts or more of the trifluoromethanesulfonic acid per part of the ortho, para-isomer. Larger amounts of the trifluoromethanesulfonic acid, combined with the large amount of phenol, additionally act as a solvent medium in which the isomerization reaction can take place.

In order that those skilled in the art may better understand how the present invention may be practiced, the following examples are given by way of illustration and not by way of limitation. All parts are by weight unless otherwise indicated.

The determination of the amount of para, para-isomer obtained in each case in the following examples was carried out by silylation of the reaction mixture containing the enhanced amounts of para, para-isomer with bis(trimethylsilyl) acetamide in the manner described by Klebe et al in J.A.C.S. 88, 3390 (1966) and then analyzed by vapor phase chromatography using a $6' \times \frac{1}{8}"$ Se-30 column with a temperature program of 200° to 300° C. at 10° C. per minute. VPC retention times for the ortho, para-isomer compound and the para, para-isomer compound are 6.2 and 7.4 minutes, respectively. All reactions in the following examples were carried out under a nitrogen atmosphere.

EXAMPLE 1

About 127.0 mg. of the dichloroethylene compound of formula VII containing 6.5% of the para, para-isomer of formula III was added to 2.0046 grams of trifluoromethanesulfonic acid containing 420.0 mg. phenol. The mixture was stirred for a period ranging up to about 15 hours during which aliquot parts were removed from the reaction mixture and analyzed by VPC in accordance with the above-described process to determine the degree of isomerization of the ortho, para-isomer to the para, para-isomer. The following Table I shows the results of the degree of isomerization as a function of time.

TABLE I

| Time (minutes) | % Ortho, Para-Isomer | % Para, Para-Isomer |
| --- | --- | --- |
| 76 | 68.8 | 30.8 |
| 125 | 47.8 | 51.8 |
| 223 | 24.0 | 74.1 |
| 275 | 14.6 | 84.3 |
| 321 | 11.0 | 88.0 |
| 399 | 5.5 | 93.7 |
| 464 | 3.5 | 95.6 |
| 15 hours | 1.0 | 98.0 |

Under the conditions of reaction described in Example 1, it was found by additional tests that as the weight ratio of the ortho, para-isomer of formula VII to phenol increased, the half life, that is the time within which to form the para, para-isomer of formula III, also increased.

EXAMPLE 2

In this example, 5.0 grams trifluoromethanesulfonic acid and 1.013 grams phenol were charged to a reaction vessel equipped with a nitrogen inlet and stirrer. Under a nitrogen blanket and with stirring, 0.51 gram of the ortho, para-isomer of formula VII containing 6.5% of the para, para-isomer of formula III was slowly added and the solution which formed was stirred for about 15 hours. Analysis of the reaction product in the manner described in Example 1 showed that all but 1% of the ortho, para-isomer had been converted to the para, para-isomer.

EXAMPLE 3

When 1.08 grams phenol and 176.8 mg. of the ortho, para-isomer of formula VII were reacted similarly as in Example 1 with the exception that 3.5 grams HF combined with $BF_3$ gas was used instead of trifluoromethanesulfonic acid, analysis of the reaction product showed that after 3 hours at 4° C. only partial isomerization occurred to about an 88:12 weight ratio of the ortho, para-isomer to the para, para-isomer.

EXAMPLE 4

When a reaction vessel equipped with nitrogen inlet was charged with 1.8164 grams trifluoromethanesulfonic acid, 2.04 grams phenol, and 237.6 mg. of the ortho, para-isomer of formula V and the solution heated at 50° C. for about 15 hours and then analyzed in the manner described above, only about 5% of the para, para-isomer of the formula

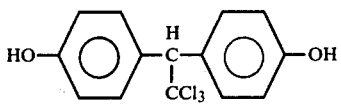

was obtained.

The above Examples 3 and 4 clearly illustrate the specificity of the trifluoromethanesulfonic acid catalyst for converting the ortho, para-dichloroethylene-compound to the para, para-dichloroethylene-compound and the lack of equivalency of trying to use the trifluoromethanesulfonic acid for converting for instance the trichloro-ethane compound of formula V to the para, para-isomer of the same dichloro-ethane compound.

EXAMPLE 5

In this example 0.0975 gram phenol and 0.02 gram of the ortho, para-isomer of formula I where X is hydrogen were added under nitrogen to 0.3738 gram trifluoromethanesulfonic acid. The solution was stirred at about 25° C. and sampled periodically and tested in the manner described in Example 1.

The following Table II shows the results of carrying out the isomerization at 25° C. for varying times.

TABLE II

| Time (minutes) at 25° C. | % Monochloro ortho, para-isomers | % $^a$Monochloro Formula II |
|---|---|---|
| 20 | 86.8 | 13.2 |
| 40 | 72.1 | 27.8 |
| 90 | 50.7 | 49.3 |
| 135 | 35.1 | 64.9 |

$^a$Where X is hydrogen

It will of course be apparent to those skilled in the art that in addition to the conditions and proportions of ingredients recited in the foregoing examples, other conditions, reactions, and proportions of ingredients may be employed without departing from the scope of the invention. Persons skilled in the art will have no difficulty in the light of the foregoing description of the invention and the working examples in determining optimum conditions which will yield maximum results in attainment of the production of the corresponding para, para-isomer.

The para, para-isomers of formula II, either in the purified state or combined with small amounts of the ortho, para-isomer of formula I, obtained in accordance with the present invention have many uses. One of the more important uses to which these compositions may be put is as intermediates in the preparation of heat-resistant polyester resins which have many uses. For instance, these chloroethylene compounds can be reacted with phthalic acids (or anhydrides) or certain phthalic acid esters (such as dimethyl terephthalate, terephthalic acid, isophthalic acid, etc.), to make polyester resins. An important use for these monomers is in the preparation of flame and heat-resistant polycarbonate resins by reacting, especially the dichloride, with carbonating agents, such as phosgene, diphenyl carbonate, etc. The polymeric compositions derived from the reaction of the dichloride here described have many applications.

These polymeric compositions may be used to form fibers, films, or molded products. Thus, either by extrusion from melt or by depositing from solution, fibers derived from these polymeric compositions may be formed and used in the preparation of various textile materials designed for clothing and similar applications.

Various fillers may be incorporated in the polymeric compositions prior to molding thereof. Among such fillers may be mentioned glass fibers, carbon black, titanium dioxide, silica, mica, bentonite, etc. Molded products derived from such a mixture of ingredients can be used as gears, handles for cooking utensils, etc. The incorporation of abrasive particles such as carborundum, diamond powder, etc., makes molded products derived from such polymeric compositions useful as grinding wheels, etc. The addition of carbon, silicon carbide, powdered metal, conducting oxides, etc., to the polymeric compositions results in the so-called resistance or semiconducting paints which have many useful applications.

What I claim as new and desire to secure by Letters Patent of the United States is:

1. The process for converting an ortho, para-isomer of the formula

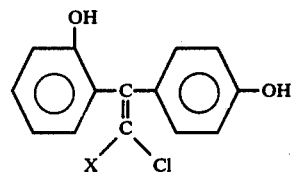

to the para, para-isomer of the formula

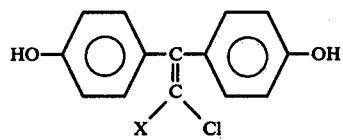

where X is a member selected from the class consisting of hydrogen and chlorine, which process comprises contacting the ortho, para-isomer with trifluoromethanesulfonic acid in the presence of phenol for a time and at a temperature sufficient to convert a substantial amount of the ortho, para-isomer to the para, para-isomer.

2. The process as in claim 1 wherein the process is carried out at a temperature from about −10° C. to below the decomposition point of the formed para, para-isomer.

3. The process as in claim 1 wherein the phenol comprises, on a weight basis, at least 1 part of the latter per part of the ortho, para-isomer.

4. The process as in claim 1 wherein the ortho, para-isomer is the dichloro compound having the formula

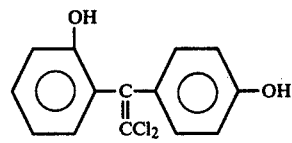

and the formed para-isomer has the formula

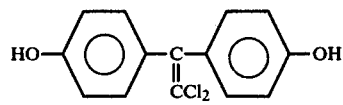

5. The process as in claim 1 wherein the ortho, para-isomer has the formula
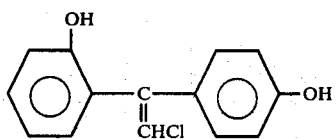
and the para, para-isomer has the formula
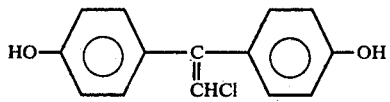
6. The process as in claim 1 wherein the trifluoromethanesulfonic acid comprises, on a weight basis, at least 0.5 part of the latter per part of the ortho, para-isomer.